United States Patent
Sato et al.

(10) Patent No.: US 11,130,982 B2
(45) Date of Patent: *Sep. 28, 2021

(54) BLOOD GLUCOSE MEASUREMENT REAGENT, SENSOR CHIP, AND BLOOD GLUCOSE METER SET

(71) Applicant: TERUMO KABUSHIKI KAISHA, Tokyo (JP)

(72) Inventors: Hiroya Sato, Tokyo (JP); Takeyuki Moriuchi, Minami-Alps (JP); Yusuke Komata, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/777,175

(22) Filed: Jan. 30, 2020

(65) Prior Publication Data

US 2020/0165660 A1    May 28, 2020

Related U.S. Application Data

(63) Continuation of application No. 16/022,967, filed on Jun. 29, 2018, now Pat. No. 10,648,015, which is a
(Continued)

(30) Foreign Application Priority Data

Feb. 4, 2016  (JP) .............................. JP2016-019689

(51) Int. Cl.
*C12Q 1/54* (2006.01)
*G01N 21/27* (2006.01)
(Continued)

(52) U.S. Cl.
CPC ............. *C12Q 1/54* (2013.01); *G01N 21/272* (2013.01); *G01N 21/78* (2013.01); *G01N 31/22* (2013.01); *C12Q 1/32* (2013.01); *G01N 21/01* (2013.01)

(58) Field of Classification Search
CPC ...... G01N 31/22; G01N 21/272; G01N 21/78; G01N 21/01; C12Q 1/54; C12Q 1/32
See application file for complete search history.

(56) References Cited

U.S. PATENT DOCUMENTS

| 4,208,346 A | 6/1980 | Conrow et al. |
| 4,892,817 A | 1/1990 | Pawlak |

(Continued)

FOREIGN PATENT DOCUMENTS

| JP | 2000-093199 A | 4/2000 |
| JP | 2006-215034 A | 8/2006 |

(Continued)

OTHER PUBLICATIONS

Office Action dated Aug. 18, 2020 in corresponding Japanese Patent Application No. 2017-565399.
(Continued)

*Primary Examiner* — Samuel P Siefke
*Assistant Examiner* — Quocan B Vo
(74) *Attorney, Agent, or Firm* — Foley & Lardner LLP

(57) ABSTRACT

A blood glucose measurement reagent includes glucose dehydrogenase; a chromogenic indicator; and an aromatic hydrocarbon having at least one sulfonic acid group.

18 Claims, 5 Drawing Sheets

Related U.S. Application Data continuation of application No. PCT/JP2016/081944, filed on Oct. 27, 2016.

(51) Int. Cl.
*G01N 31/22* (2006.01)
*G01N 21/78* (2006.01)
*C12Q 1/32* (2006.01)
*G01N 21/01* (2006.01)

(56) References Cited

U.S. PATENT DOCUMENTS

| | | | |
|---|---|---|---|
| 5,082,770 A * | 1/1992 | Okada | C12N 9/0008 435/18 |
| 6,200,773 B1 | 3/2001 | Ouyang et al. | |
| 2003/0044316 A1 | 3/2003 | Hirai et al. | |
| 2003/0166295 A1 | 9/2003 | Fukuoka et al. | |
| 2003/0180183 A1 | 9/2003 | Fukuoka et al. | |
| 2003/0195134 A1 | 10/2003 | Vandijk et al. | |
| 2008/0125471 A1 | 5/2008 | Albarella et al. | |
| 2009/0047601 A1 * | 2/2009 | Iwai | B41C 1/1008 430/285.1 |
| 2014/0107048 A1 | 4/2014 | Pan et al. | |
| 2014/0107059 A1 | 4/2014 | Pan et al. | |

FOREIGN PATENT DOCUMENTS

| | | |
|---|---|---|
| JP | 2008-526990 A | 7/2008 |
| JP | 2008-197077 A | 8/2008 |
| JP | 4381463 B2 | 12/2009 |
| WO | WO-2006/023927 A1 | 3/2006 |
| WO | WO-2006/076619 A1 | 7/2006 |
| WO | WO-2014/049704 A1 | 4/2014 |

OTHER PUBLICATIONS

International Searching Authority, "Search Report," issued in connection with International Patent Application No. PCT/JP2016/081944, dated Jan. 31, 2017.

International Searching Authority, "Written Opinion," issued in connection with International Patent Application No. PCT/JP2016/081944, dated Jan. 31, 2017.

Extended European Search Report dated Sep. 25, 2019 for counterpart European Application No. 16889361.

* cited by examiner

BLOOD GLUCOSE MEASUREMENT REAGENT, SENSOR CHIP, AND BLOOD GLUCOSE METER SET

CROSS-REFERENCE TO RELATED APPLICATIONS

The present application is a continuation of U.S. patent application Ser. No. 16/022,967, filed on Jun. 29, 2018, which is a bypass continuation of PCT Application No. PCT/JP2016/081944, filed on Oct. 27, 2016, which claims priority to Japanese application number 2016-019689, filed on Feb. 4, 2016. The contents of these applications are hereby incorporated by reference in their entireties.

BACKGROUND ART

The present disclosure relates to a blood glucose measurement reagent, a sensor chip, and a blood glucose meter set, and particularly relates to a blood glucose measurement reagent, a sensor chip, and a blood glucose meter set that can prevent or reduce the risk of color development before blood application and also can increase the color development speed after blood application even when the blood as an analyte is whole blood.

Conventionally, a blood glucose meter for measuring glucose components in blood has been widely used (see JP 2006-215034 A, for example).

According to the blood glucose meter, blood (whole blood) is injected to a sensor chip which has an enzyme and a reagent containing a chromogenic indicator (dye-forming substance) (see JP 4381463 B2, for example) and coloration level at the time of a reaction between the reagent and blood (whole blood) is photometrically (optically) measured so that the glucose components in blood can be measured (see WO 2014/049704 A, for example).

SUMMARY

However, the chromogenic indicator (dye-forming substance) used for the measurement of blood glucose level in whole blood (for example, tetrazolium salt like WST-4) has a problem that, due to the presence of a buffer agent included in the reagent, color development is shown even before blood application.

To solve the above issue, determination has been made for not adding a buffer agent. However, when the buffer agent is not added, there is a problem that the change speed of color development (i.e., absorbance) after blood application is slowed down, and, even after a predetermined time following the blood application, a change in color development (i.e., absorbance) is continuously shown.

An object of certain embodiments of the present disclosure is to provide a blood glucose measurement reagent, a sensor chip, and a blood glucose meter set that can prevent or reduce the risk of color development before blood application and also can increase the color development speed after blood application.

According to a first embodiment, a blood glucose measurement reagent includes: an enzyme having glucose as a substrate; a mediator; and a chromogenic indicator, wherein the blood glucose measurement reagent additionally includes an aromatic hydrocarbon having at least one sulfonic acid group.

Accordingly, not only the risk of color development before blood application can be prevented or reduced but also the color development speed after blood apply can be increased.

Furthermore, in the present specification, an "aromatic hydrocarbon" is defined as a kind of carbocyclic compounds (i.e., among cyclic compounds, compound containing only carbon atoms in the ring) that are different from heterocyclic compounds, and that do not have any amine.

In one aspect, the aromatic hydrocarbon has two or more sulfonic acid groups.

By placing the sulfonic acid groups over the entire periphery of an aromatic ring of the aromatic hydrocarbon, each of the hydrophilic moiety and hydrophobic moiety is not localized in the aromatic hydrocarbon molecule so that the reagent can easily become wetted by (be sufficiently mixed with) blood.

In one aspect, the aromatic hydrocarbon is disodium 1,3-benzene disulfonate or trisodium naphthalene-1,3,6-trisulfonate.

Furthermore, although disodium 1,3-benzene disulfonate and trisodium naphthalene-1,3,6-trisulfonate have no buffering capacity, the buffering capacity of blood itself can be used for reaction in a neutral pH range.

In one aspect, the content of the aromatic hydrocarbon is 30% by mol or more.

In one aspect, a tetrazolium salt is additionally contained as the chromogenic indicator.

According to a second embodiment, a sensor chip includes a supply port through which blood is supplied, a flow path having the supply port formed at one end, and a reagent which is provided in the flow path. The sensor chip is mountable on a blood glucose meter for measuring the blood glucose level in the blood, in which the reagent is the blood glucose measurement reagent described with respect to the first embodiment above.

According to a third embodiment, a blood glucose meter set includes the sensor chip described above with respect to the second embodiment, and a blood glucose meter for measuring the blood glucose level in blood, in which the blood glucose meter includes a light illuminating part for illuminating a reaction product of the blood and the reagent with light, a light receiving part for receiving measured light which has been transmitted through the reaction product or reflected from the reaction product, and a processing part for processing a signal resulting from the measured light.

According to certain embodiments, a blood glucose measurement reagent, a sensor chip, and a blood glucose meter set that can prevent or reduce the risk of color development before blood application and also can increase the color development speed after blood application can be provided.

DETAILED DESCRIPTION (Blood Glucose Measurement Reagent)

Figure 1:
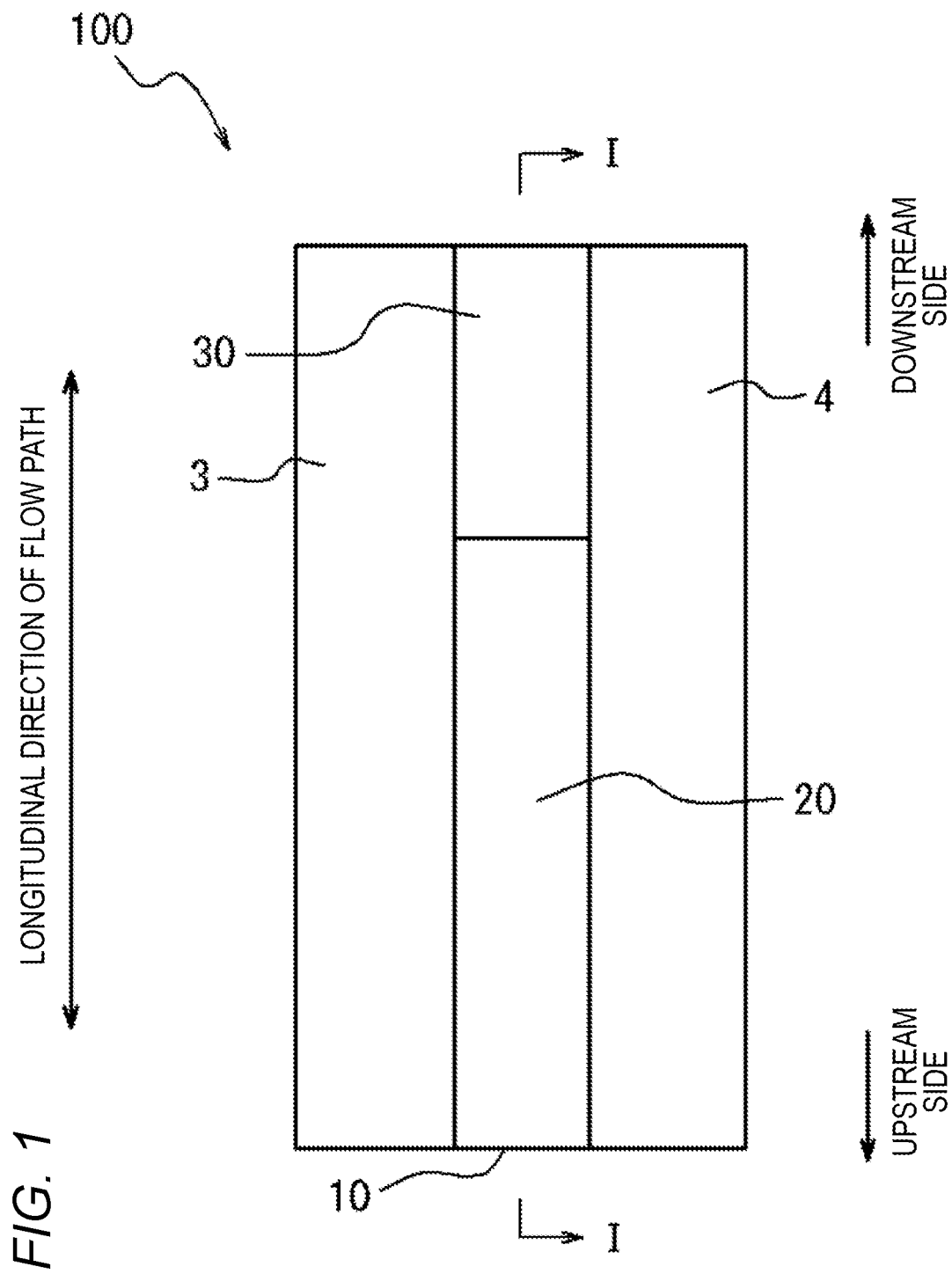
FIG. 1 is a planar view illustrating the sensor chip according to one embodiment.

The blood glucose measurement reagent according to certain embodiment includes at least an enzyme, a mediator, a chromogenic indicator (dye-forming substance), and an aromatic hydrocarbon (arene). Furthermore, the blood glucose measurement reagent according to certain embodiments is achieved by additionally including, if necessary, other components like transition metal salt.

Furthermore, D-glucose in blood and the mediator (for example, m-PMS which will be described later) react with an enzyme (for example, GDH which will be described later), and according to the reaction, the chromogenic indicator (for example, TWT-4 which will be described later) yields color development.

<Aromatic Hydrocarbon>

The aromatic hydrocarbon is not particularly limited as long as it is an aromatic hydrocarbon having at least one sulfonic acid group, and it can be suitably selected depending on the purpose. Examples thereof include sodium benzene sulfonate (see, the following Structural Formula (1)), disodium1,3-benzene disulfonate (see, the following Structural Formula (2)), trisodium 1,3,5-benzene trisulfonate (see, the following Structural Formula (3)), trisodium naphthalene-1,3,6-trisulfonate (see, the following Structural Formula (4)), and trisodium anthracene-1,3,6-trisulfonate (see, the following Structural Formula (5)). They may be used either singly or in combination of two or more types thereof.

Among them, the aromatic hydrocarbon having two or more sulfonic acid groups (for example, disodium1,3-benzene disulfonate and trisodium naphthalene-1,3,6-trisulfonate) is preferable from the viewpoint that the color development speed after blood application can be further increased. Herein, those having the larger number of sulfonic acid groups (ions) can have a reduced activity of a surfactant while having enhanced hydrophilicity of the aromatic hydrocarbon, and thus the color development speed can be further increased even when whole blood is used as a sample. This effect can be obtained even at low content. Furthermore, there is no adverse effect on the stability even when the number of the sulfonic acid groups contained in the aromatic hydrocarbon is high.

[0019]

[Chemical Formula 1]

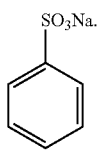

Structural Formula (1)

[0020]

[Chemical Formula 2]

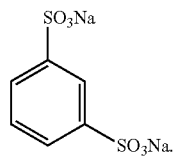

Structural Formula (2)

[0021]

[Chemical Formula 3]

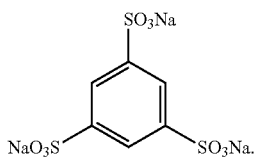

Structural Formula (3)

[0022]

[Chemical Formula 4]

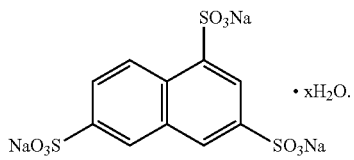

Structural Formula (4)

[0023]

[Chemical Formula 5]

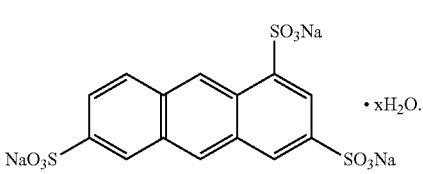

Structural Formula (5)

The content of the aromatic hydrocarbon is not particularly limited, and it can be suitably selected depending on the purpose. However, it is preferably 30% by mol or more, more preferably 50% by mol or more, and particularly preferably 70% by mol to 80% by mol.

The concentration of the aromatic hydrocarbon at the time of a blood analyte reaction is not particularly limited, and it can be suitably selected depending on the purpose. However, it is preferably 50 mM or more, more preferably 100 mM or more, and particularly preferably 250 mM to 400 mM.

As the content of the aromatic hydrocarbon or the concentration thereof at the time of a blood analyte reaction is within the preferred range, more preferred range, or particularly preferred range, the risk of having color development before blood application can be surely prevented or reduced and also the color development speed after blood application can be surely increased.

<Enzyme>

The enzyme plays a role of reacting with glucose in blood, withdrawing electrons from the glucose, or the like, for example.

The enzyme is not particularly limited as long as it has glucose as a substrate, and it can be suitably selected depending on the purpose. Examples thereof include glucose dehydrogenase (GDH) and glucose oxidase (GOD). They may be used either singly or in combination of two or more types thereof.

Among them, glucose dehydrogenase (GDH) is preferable from the viewpoint that it can be easily combined with a tetrazolium salt.

Furthermore, although the pH region in which the reaction of glucose dehydrogenase (GDH) progresses smoothly (i.e., optimum pH region) is near neutral region (i.e., pH of about 6.5 to 7.0), the optimum pH varies depending on the enzyme. For example, because "glycine-hydrochloric acid" and "sodium acetate" that are used as a buffer agent (i.e., buffer) used in embodiments of JP 4381463 B2 are acidic, they are not suitable for glucose dehydrogenase (GDH) which has the optimum pH region near neutral region (i.e., pH of about 6.5 to 7.0).

The enzyme concentration at the time of a blood analyte reaction is not particularly limited, and it can be suitably selected depending on the purpose. However, it is preferably 1 U/µL or more, more preferably 4 U/µL or more, and particularly preferably 8 U/µL to 20 U/µL.

As the concentration at the time of a blood analyte reaction is within the preferred range, more preferred range, or particularly preferred range, the reaction can be completed within a short time.

<Mediator>

The mediator plays a role of (i) promoting a reaction between an enzyme and glucose in blood, (ii) receiving the electrons that are withdrawn from glucose by the enzyme and then delivering them to a chromogenic indicator (dye-forming substance), or the like.

The mediator is not particularly limited, and it can be suitably selected depending on the purpose. As for the mediator, 5-methylphenazinium methyl sulfate (PMS), 1-methoxy-5-methylphenaziniummethyl sulfate (mPMS), NAD, FAD, PQQ, potassium ferricyanide, or the like can be selected. They may be used either singly or in combination of two or more types thereof.

Among them, 1-methoxy-5-methylphenazinium methyl sulfate (mPMS) is preferable from the viewpoint that it is excellent in term of both the reactivity and stability.

The content of the mediator is not particularly limited, and it can be suitably selected depending on the purpose. The content of the mediator is preferably 0.01% by mol or more, more preferably 0.1% by mol or more, and particularly preferably 0.3% by mol to 3% by mol.

The concentration of the mediator at the time of a blood analyte reaction is not particularly limited, and it can be suitably selected depending on the purpose. The concentration of the mediator at the time of a blood analyte reaction is preferably 0.1 mM or more, more preferably 0.5 mM or more, and particularly preferably 1 mM to 10 mM.

As the content of the mediator or the concentration thereof at the time of a blood analyte reaction is within the preferred range, more preferred range, or particularly preferred range, the reaction can be completed within a short time.

<Chromogenic Indicator>

The chromogenic indicator (dye-forming substance) (i.e., reduction type indicator) can play a role of showing color development by receiving electrons or hydrogen peroxides (i.e., indicator being reduced) that are generated according to a reaction between the enzyme and glucose, for example.

The chromogenic indicator is not particularly limited, and it can be suitably selected depending on the purpose. Examples thereof include a tetrazolium salt (for example, WST-4, WST-1, WST-5, MTS, MTT, and tetrazolium salt (A)), sodiumphosphomolybdate, indigo carmine, dichloroindophenol, and resazurin. They may be used either singly or in combination of two or more types thereof.

Among them, a tetrazolium salt having a benzothiazoyl group is preferable, and the tetrazolium salt (A) and 2-(2-benzothiazolyl)-3-(4-carboxy-2-methoxyphenyl)-5-[4-[(2-sodiosulfoethyl)carbamoyl]phenyl]-2H-tetrazol-3-ium (WST-4) are particularly preferable in that they have a favorable color development spectrum and high solubility.

Chemical structure of the tetrazolium salt (A) is shown below.

[Chemical Formula 6]

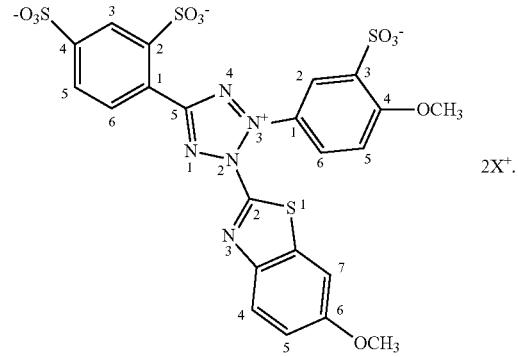

In the formula, X=Na.

The content of the chromogenic indicator is not particularly limited, and it can be suitably selected depending on the purpose. However, it is preferably 5% by mol or more, more preferably 15% by mol or more, and particularly preferably 30% by mol to 50% by mol.

The concentration of the chromogenic indicator at the time of a blood analyte reaction is not particularly limited, and it can be suitably selected depending on the purpose. However, it is preferably 10 mM or more, more preferably 50 mM or more, and particularly preferably 100 mM to 200 mM.

As the content of the chromogenic indicator or the concentration thereof at the time of a blood analyte reaction is within the preferred range, more preferred range, or particularly preferred range, even a blood glucose level of high concentration can be dealt with.

<Transition Metal Salt>

In a case in which the chromogenic indicator is a tetrazolium salt, it is also possible that a transition metal salt (transition metal ion) and a tetrazolium salt are subjected to a chelate reaction, and a chelate complex is formed for having color development. The transition metal salt can be suitably selected depending on the purpose as long as it can generate ions in aqueous liquid (for example, water, buffer solution, blood, and body fluid). However, it is preferably chloride, bromide, nitrate, sulfate, or organic acid salt of nickel or cobalt.

(Sensor Chip)

The sensor chip according to certain embodiments is described in detail below.

FIG. 1 is a planar view illustrating the sensor chip according to one embodiment. Furthermore, FIG. 2 is a cross-sectional view along line I-I of FIG. 1.

Figure 2:
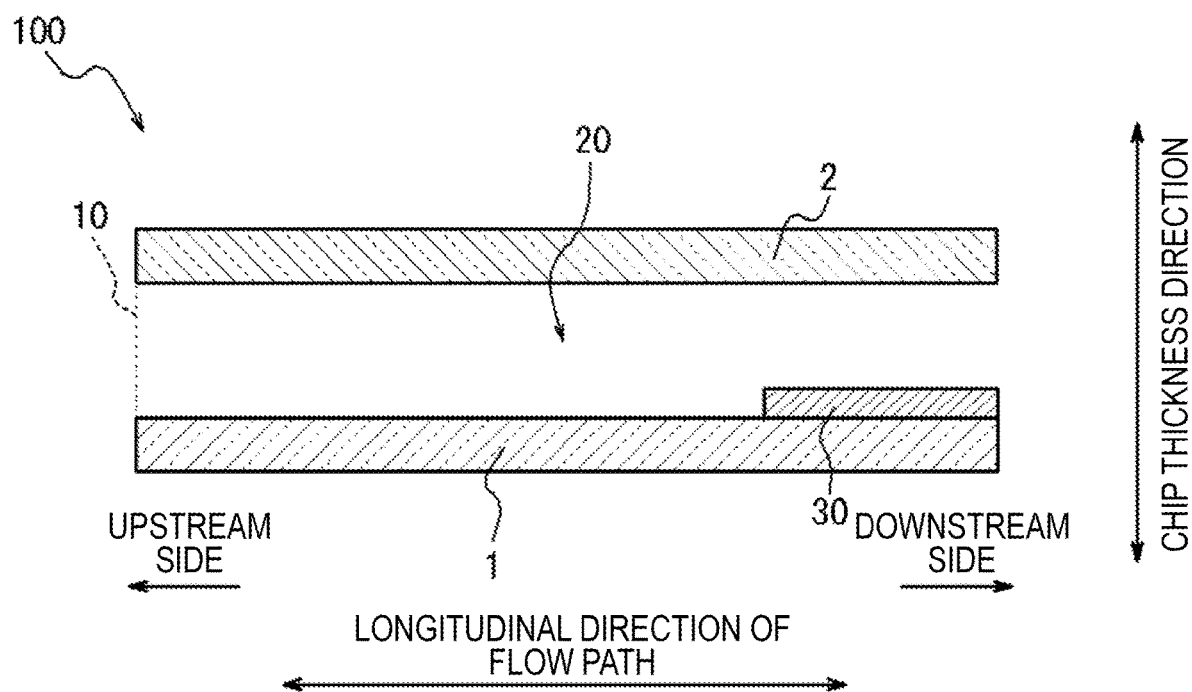
FIG. 2 is a cross-sectional view along line I-I of FIG. 1.

As illustrated in FIG. 1 and FIG. 2, the sensor chip 100 in the present embodiment is provided with a support port 10, a flow path 20, and a reagent layer 30, and it can be mounted on a blood glucose meter that will be described later.

Details of each member of the sensor chip 100 of the present embodiment and characteristic parts consisting of each member are described below.

<<Support port 10, Flow path 20, and Reagent layer 30>>

As illustrated in FIG. 1 and FIG. 2, the sensor chip 100 is provided with a first base 1 for forming a bottom surface part, a second base 2 for forming a top surface part, and adhesion parts 3 and 4 that are provided between the first base 1 and the second base 2 and also at both ends in the width direction which is perpendicular to the chip thickness direction.

As such, with regard to the adhesion parts 3 and 4, while having a spacer with any thickness (not illustrated in the drawings) inserted between the first base 1 and the second base 2, the first base 1 and the second base 2 are attached to each other so that a void with a predetermined size is formed between the first base 1 and the second base 2. This void with the predetermined size serves as the flow path 20 having the support port 10 formed at one end thereof, and thus blood is allowed to flow into the sensor chip 100. Furthermore, inside the flow path 20, the reagent layer 30 is provided. Although the reagent layer 30 is formed on the first base 1 in FIG. 1 and FIG. 2, it is not limited thereto, and it is acceptable that the reagent layer 30 is provided inside the flow path 20 without blocking the flow path 20.

The material of the first base 1 can be suitably selected depending on the purpose (i.e., illuminating light and receiving light), and examples thereof include a transparent organic resin material such as polyethylene terephthalate (PET), polymethyl methacrylate, polystyrene, cyclic polyolefin, cyclic olefin copolymer, or polycarbonate; and a transparent inorganic material such as glass and quartz.

The material of the second base 2 can be suitably selected depending on the purpose (i.e., illuminating light and receiving light), and examples thereof include a transparent organic resin material like a polyester film subjected to a hydrophilicizing treatment (e.g., 3M hydrophilicized film).

The thicknesses of adhesion parts 3 and 4 are suitably adjusted so as to have a desired value of the length of the flow path 20 in the chip thickness direction. For example, it is possible that a spacer with any thickness is disposed between a first base and a second base followed by adhesion or melt-adhesion, or a double-sided tape also functioning as a spacer is used as an adhesive member for attaching a first base and a second base.

—Reagent Layer 30—

The reagent layer 30 consists of the blood glucose measurement reagent described above.

—Method for Producing Reagent Layer 30—

The method for producing the above reagent layer structure includes at least a coating step and a drying step, and if necessary, a step other than those steps.

—Coating Step—

The coating step is a step for coating a coating liquid containing the blood glucose measurement reagent.

The coating method is not particularly limited, and it can be suitably selected depending on the purpose. Examples thereof include spray coating, inkjet method, screen printing, and gravure printing. They may be used either singly or in combination of two or more types thereof.

—Drying Step—

The drying step is a step for drying the coated coating liquid. The drying temperature and drying time of the drying step can be suitably selected depending on the purpose.

(Blood Glucose Meter Set)

Next, descriptions are given for the blood glucose meter set as according to certain embodiments.

The blood glucose meter set according to one embodiment includes the aforementioned sensor chip, and a blood glucose meter on which the sensor chip is mounted, for measuring glucose components in blood.

Below, descriptions are given for a blood glucose meter set that is provided with a transmission photometry blood glucose meter for measuring the light transmitted through a reaction product of blood and a chromogenic indicator as a blood glucose measurement reagent, but the present invention is not limited thereto. For example, it can be also a blood glucose meter set provided with a reflection photometry blood glucose meter for measuring the light reflected from the reaction product described above.

Figure 3:
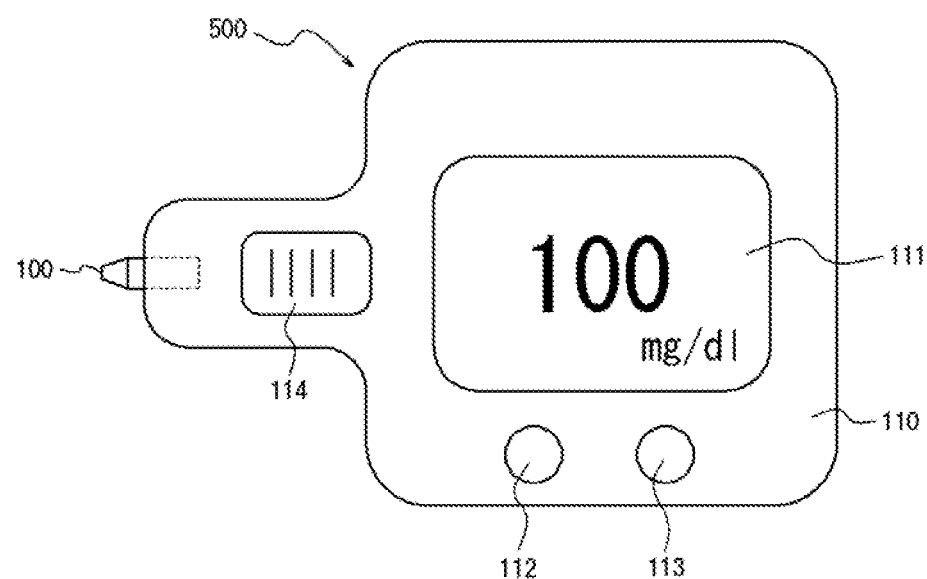
FIG. 3 is a planar view illustrating the blood glucose meter set according to one embodiment.

FIG. 3 illustrates a blood glucose meter set 500 according to one embodiment. The blood glucose meter set 500 is provided with a blood glucose meter 110 and a sensor chip 100.

The sensor chip 100 is to be mounted on the tip part of the blood glucose meter 110. The blood glucose meter 110 is provided with a display 111 for displaying measurement results, contents of the operation, or the like, a power button 112 for instructing on and off of the blood glucose meter 110, an operation button 113, and a release lever 114 for releasing the sensor chip 100. The display 111 consists of a liquid crystal, an LED, or the like.

Figure 4:
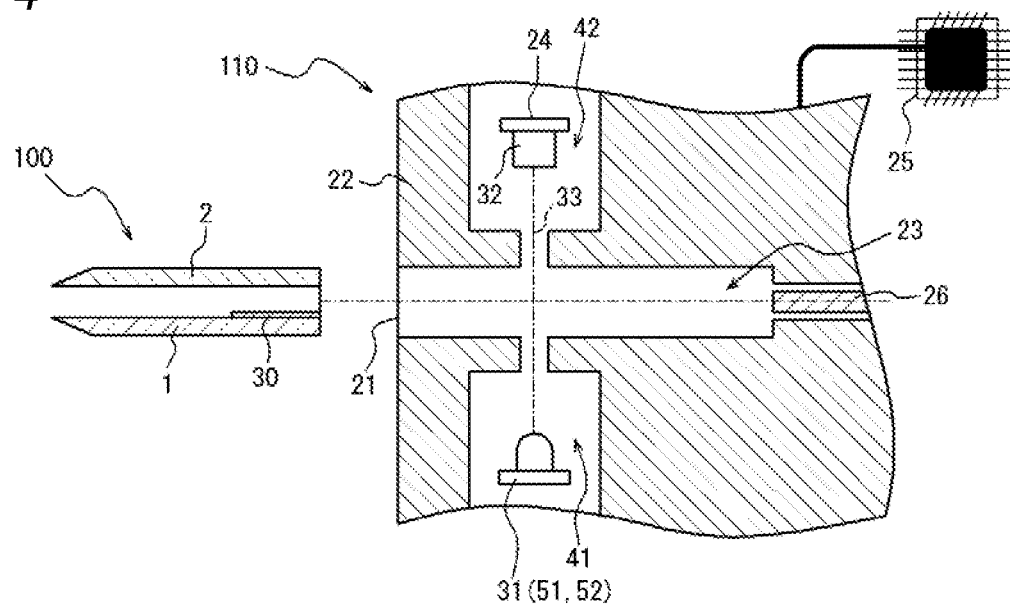
FIG. 4 is a longitudinal cross-sectional view illustrating the blood glucose meter and sensor chip of the blood glucose meter set illustrated in FIG. 3.

FIG. 4 is a longitudinal cross-sectional view illustrating each of the tip part of the blood glucose meter 110 and the sensor chip 100 of the blood glucose meter set 500. For mounting the sensor chip 100 on the blood glucose meter 110, a mounting part 22 having an opening part 21 formed at the tip part of the blood glucose meter 110 is provided, and a mounting hole 23 for mounting the sensor chip 100 inside the blood glucose meter 110 is constructed. Furthermore, inside the blood glucose meter 110, an optical measurement part 24 for measuring glucose components (i.e., blood glucose level) of the blood collected on the sensor chip 100 is provided. Furthermore, the blood glucose meter 110 is provided with a processing part 25 for calculating the blood glucose level by processing the signal resulting from measured light, and an eject pin 26 for releasing the sensor chip 100 in conjunction with the release lever 114 (see, FIG. 3). Descriptions are given for each constitution below.

At the time of the measurement, the sensor chip 100 is mounted in the mounting hole 23. The mounting operation is carried out manually by a user. Although it is not illustrated, in order to minimize any irregularity of a mounting position that is caused by manual operation, it is preferable to provide a lock device or the like for fixing the sensor chip 100 at a predetermined position inside the mounting hole 23.

The optical measurement part 24 is provided with a light illuminating part 31 for illuminating a reaction product of blood and a chromogenic indicator (dye-forming substance) as a blood glucose measurement reagent with light, and light receiving part 32 for receiving the light transmitted through the reaction product as measured light. In the present embodiment, a light emitting diode (LED) is used for the light illuminating part 31, but it can be also a halogen lamp, laser, or the like. For the light receiving part 32, a photodiode (PD) is used, for example. The light receiving part 32 can be any one that can convert the received light to a certain signal, and it can be also CCD, CMOS, or the like.

According to the present embodiment, the light illuminating part 31 has a first light emitting element 51 for emitting light with a first wavelength and a second light emitting element 52 for emitting light with a second wavelength that is different from the first wavelength. Herein, the first wavelength indicates a wavelength for detecting the degree of color development according to blood glucose amount, and it is within a wavelength region of 600 to 900 nm, for example. The second wavelength indicates a wavelength for detecting the red blood cell concentration in blood, and it is within a wavelength region of 510 to 590 nm, for example.

Descriptions are given for the arrangement and positional relationship of the light illuminating part 31 and the light receiving part 32. Inside the blood glucose meter 110, a first space 41 and a second space 42 are created. The light illuminating part 31 is disposed in the first space 41 and the light receiving part 32 is disposed in the second space 42, respectively. In a state in which the sensor chip 100 is not mounted on the blood glucose meter 110, the first space 41 and the second space 42 face each other while having the mounting hole 23 therebetween (see, FIG. 4). In a state in which the sensor chip 100 is mounted on the blood glucose meter 110, the first space 41 and the second space 42 face each other while having therebetween an area in which the reagent layer 30 on the sensor chip 100 is hold. Furthermore, to minimize the energy loss of the illumination light 33, the light illuminating part 31 is preferably disposed at an area in which the bottom surface of the sensor chip 100 can be perpendicularly illuminated with the illumination light 33.

Although not illustrated, in a case in which a halogen lamp is used for the light illuminating part 31 to have white light illumination, it is also possible to have a method in which a spectral filter is disposed to extract only specific wavelength as the illumination light 33. It is also suitable to have a method of having a condenser lens to provide effective performance with low energy illumination.

Embodiments of the present disclosure are described in further detail below, but the present invention is not limited to the embodiments below.

Embodiments

Embodiment 1

<Preparation of Aqueous Reagent Solution>

First, an aqueous reagent solution (pH 6.5) containing 4 U/μL glucose dehydrogenase (GDH, manufactured by TOYOBO CO., LTD.) as an enzyme, 1 mM 1-methoxy-5-methylphenazinium methyl sulfate (mPMS, manufactured by DOJINDO LABORATORIES) as a mediator, 100 mM 2-benzo-thiazolyl-3-(4-carboxy-2-methoxyphenyl)-5-[4-(2-sulfoethylcarbamoyl)phenyl]-2H-tetrazolium (WST-4, manufactured by DOJINDO LABORATORIES) as a chromogenic indicator, and 250 mM trisodium naphthalene-1,3,6-trisulfonate (TSN, manufactured by Tokyo Chemical Industry Co., Ltd.) as an aromatic hydrocarbon was prepared.

<Production of the Sensor Chip>

The prepared aqueous reagent solution was applied on a polyethylene terephthalate (PET) film (manufacturer's name: Toray Industries, Inc., trade name: Lumirror T60, thickness of 188 μm) and then dried for 10 minutes at 25° C.

After drying, to the PET film having a reagent layer formed thereon, a cover film of which the material is a hydrophilicized polyester film (manufacturer's name: 3M Company, trade name: hydrophilicized polyester film 9901P, thickness of 100 μm) was mounted while a spacer and a double-sided tape as an adhesion part (manufacturer's name: 3M Company, trade name: polyester film base, double-sided adhesive tape 9965, thickness of 80 μm) were inserted therebetween, and thus the sensor chip illustrated in FIGS. 1 and 2 was produced.

<Preparation of Blood Analyte>

Glucose solution having high concentration (40 g/dL) was added to blood (whole blood, hematocrit (Ht) 40) to prepare a blood analyte having glucose concentration of 100 mg/dL.

<Absorbance Measurement After Analyte Application>

The blood analyte which has been prepared above (3 mm$^3$) was applied onto the sensor chip prepared above, and by using a UV and visible spectrophotometer, absorbance was measured (wavelength for measurement: 650 nm). The results are shown in Table 1 and FIG. 5.

Figure 5:
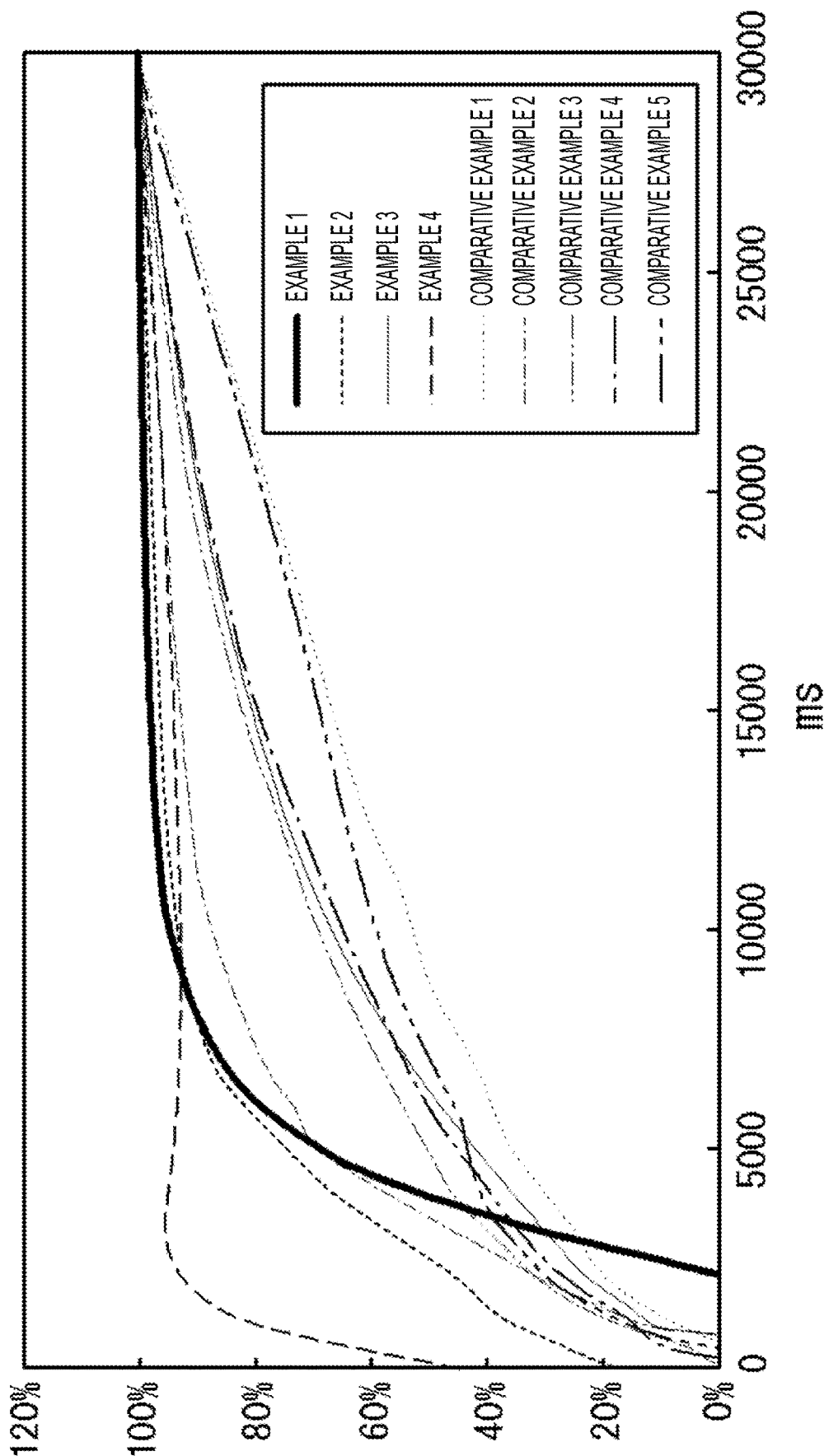
FIG. 5 is a graph illustrating the color development speed of each reagent (Embodiments 1 to 4 and Comparative Embodiments 1 to 5), in which the vertical axis indicates the absorbance index (i.e., index when the color development amount after 30 seconds is set at 100%) and the horizontal axis indicates the time after application (ms: milliseconds).

Furthermore, FIG. 5 is a graph illustrating the color development speed (in time course), in which the vertical axis indicates the absorbance index (i.e., color development amount after 30 seconds is set at 100%) and the horizontal axis indicates the time after application (ms: milliseconds). The time until completion of color development was evaluated in terms of the time from 0 second to time at which the color development amount is 100%.

<Absorbance Measurement After Thermal Acceleration Test>

By using a UV and visible spectrophotometer, absorbance after application of distilled water (3 mm$^3$) was measured for each sensor chip immediately after the production (i.e., initial), after storage at room temperature (for 3 days), and after a thermal acceleration test (60° C., for 3 days) (wavelength for measurement: 650 nm to 750 nm). With regard to those absorbances of the sensor chip, the result obtained as a difference of the absorbance with respect to a sensor chip immediately after the production (i.e., initial) is shown in Table 1 and FIG. 6.

Figure 6:
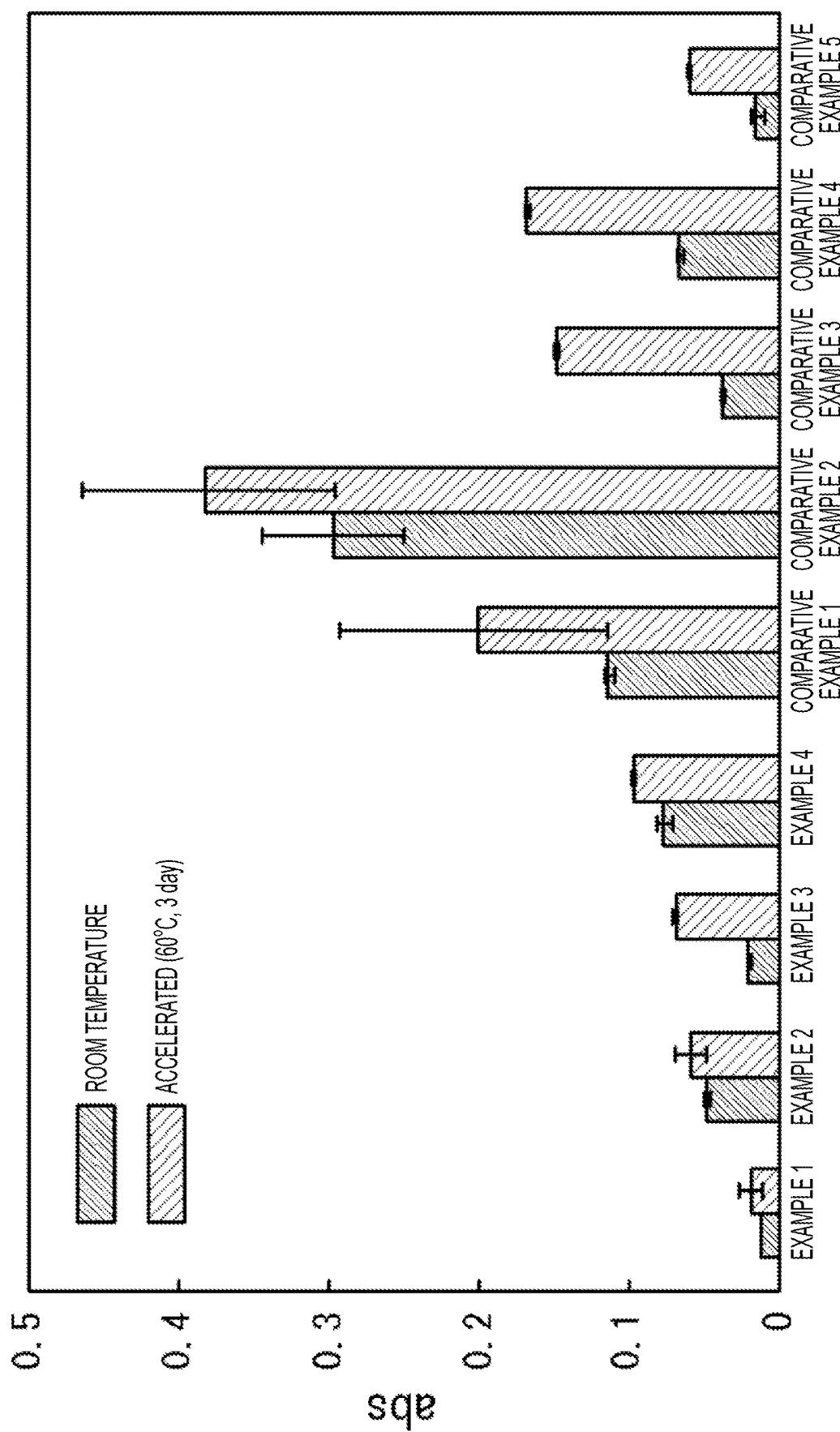
FIG. 6 is a graph illustrating the storage stability of each reagent (Embodiments 1 to 4 and Comparative Embodiments 1 to 5) before blood application, in which the vertical axis indicates absorbance (abs).

Furthermore, FIG. 6 is a graph illustrating the storage stability of a sensor chip before applying blood, in which the vertical axis indicates absorbance (abs).

Embodiment 2

Preparation of an aqueous reagent solution, production of a sensor chip, preparation of an analyte, absorbance measurement after analyte application, and absorbance measurement after thermal acceleration test were carried out in the same manner as Embodiment 1 except that, instead of carrying out the preparation of an aqueous reagent solution by using trisodium naphthalene-1,3,6-trisulfonate (TSN, manufactured by Tokyo Chemical Industry Co., Ltd.) in Embodiment 1, the preparation of an aqueous reagent solution was carried out by using disodium 1,3-benzene disulfonate (DSB, manufactured by Alfa Aear). The evaluation results are illustrated in FIGS. 5 and 6.

Embodiment 3

Preparation of an aqueous reagent solution, production of a sensor chip, preparation of an analyte, absorbance measurement after analyte application, and absorbance measurement after thermal acceleration test were carried out in the same manner as Embodiment 1 except that, instead of carrying out the preparation of an aqueous reagent solution by using trisodium naphthalene-1,3,6-trisulfonate (TSN, manufactured by Tokyo Chemical Industry Co., Ltd.) in Embodiment 1, the preparation of an aqueous reagent solution was carried out by using sodium benzene sulfonate (BS, manufactured by Tokyo Chemical Industry Co., Ltd.). The evaluation results are shown in Table 1, and FIGS. 5 and 6.

Embodiment 4

Production of a sensor chip, preparation of an analyte, absorbance measurement after analyte application, and absorbance measurement after thermal acceleration test were carried out in the same manner as Embodiment 1 except that "Preparation of aqueous reagent solution" of Embodiment 1 was carried out as described below, and the absorbance measurement in "Absorbance measurement after analyte application" was carried out at 630 nm to 900 nm. The evaluation results are shown in Table 1, and FIGS. 5 and 6.

When the tetrazolium salt A is used as a chromogenic indicator, rapid progress of the reaction was shown simultaneously with the start of the measurement, and the color development was completed at 5 seconds, approximately. The color development speed and sensitivity were both favorable in Embodiment 4.

<Preparation of Aqueous Reagent Solution>

First, an aqueous reagent solution (pH of 6.5) and containing 4 U/μL glucose dehydrogenase (GDH, manufactured by TOYOBO CO., LTD.) as an enzyme, 1 mM 1-methoxy-5-methylphenazinium methyl sulfate (mPMS, manufactured by DOJINDO LABORATORIES) as a mediator, 100 mM tetrazolium salt A (manufactured by Terumo Corporation) as a chromogenic indicator (dye-forming substance), 200 mM of nickel ions as a transition metal ion, and 250 mM disodium 1,3-benzene disulfonate (DSB, manufactured by Alfa Aear) as an aromatic hydrocarbon was prepared.

Comparative Embodiment 1

Preparation of an aqueous reagent solution, production of a sensor chip, preparation of an analyte, absorbance measurement after analyte application, and absorbance measurement after thermal acceleration test were carried out in the same manner as Embodiment 1 except that, instead of carrying out the preparation of an aqueous reagent solution by adding trisodium naphthalene-1,3,6-trisulfonate (TSN, manufactured by Tokyo Chemical Industry Co., Ltd.) in Embodiment 1, the preparation of an aqueous reagent solution was carried out without adding trisodium naphthalene-1,3,6-trisulfonate (TSN, manufactured by Tokyo Chemical Industry Co., Ltd.). The evaluation results are shown in Table 1, and FIGS. 5 and 6.

Comparative Embodiment 2

Preparation of an aqueous reagent solution, production of a sensor chip, preparation of an analyte, absorbance measurement after analyte application, and absorbance measurement after thermal acceleration test were carried out in the same manner as Embodiment 1 except that, instead of carrying out the preparation of an aqueous reagent solution (pH 6.5) by using trisodium naphthalene-1,3,6-trisulfonate (TSN, manufactured by Tokyo Chemical Industry Co., Ltd.) in Embodiment 1, the preparation of an aqueous reagent solution (pH 7.0) was carried out by using 3-morpholino-propanesulfonic acid (MOPS, manufactured by DOJINDO LABORATORIES). The evaluation results are shown in Table 1, and FIGS. 5 and 6.

As Comparative Embodiment 2, when a good buffer (i.e., buffer having buffer capacity near neutral region and having free amine) like MOPS is used, there was a tendency that the color development gradually starts during the preparation of an aqueous reagent solution, and significantly increased absorbance is obtained in a state in which blood is yet to be applied (i.e., blank).

Comparative Embodiment 3

Preparation of an aqueous reagent solution, production of a sensor chip, preparation of an analyte, absorbance measurement after analyte application, and absorbance measurement after thermal acceleration test were carried out in the same manner as Embodiment 1 except that, instead of carrying out the preparation of an aqueous reagent solution (pH 6.5) by using trisodium naphthalene-1,3,6-trisulfonate (TSN, manufactured by Tokyo Chemical Industry Co., Ltd.) in Embodiment 1, the preparation of an aqueous reagent solution was carried out by using sodium isethionate (manufactured by Tokyo Chemical Industry Co., Ltd.). The evaluation results are shown in Table 1, and FIGS. 5 and 6.

Comparative Embodiment 4

Preparation of an aqueous reagent solution, production of a sensor chip, preparation of an analyte, absorbance measurement after analyte application, and absorbance measurement after thermal acceleration test were carried out in the same manner as Embodiment 1 except that, instead of carrying out the preparation of an aqueous reagent solution (pH 6.5) by using trisodium naphthalene-1,3,6-trisulfonate (TSN, manufactured by Tokyo Chemical Industry Co., Ltd.) in Embodiment 1, the preparation of an aqueous reagent solution (pH 7.0) was carried out by using phosphate buffer solution (manufactured by Wako Pure Chemical Industries Ltd.). The evaluation results are shown in Table 1, and FIGS. 5 and 6.

As Comparative Embodiment 4, when a phosphate buffer (i.e., buffer having no free amine), which is not a good buffer, is used, there was a tendency that slower color development speed is yielded even though the storage stability before blood application is favorable.

Comparative Embodiment 5

Preparation of an aqueous reagent solution, production of a sensor chip, preparation of an analyte, absorbance measurement after analyte application, and absorbance measurement after thermal acceleration test were carried out in the same manner as Embodiment 1 except that, instead of carrying out the preparation of an aqueous reagent solution (pH 6.5) by using trisodium naphthalene-1,3,6-trisulfonate (TSN, manufactured by Tokyo Chemical Industry Co., Ltd.) in Embodiment 1, the preparation of an aqueous reagent solution was carried out by using trehalose (manufactured by HAYASHIBARA CO., LTD.). The evaluation results are shown in Table 1, and FIGS. 5 and 6.

As Comparative Embodiment 5, when trehalose easily soluble in water but having no buffer capacity is used, there was a tendency that slower color development speed is yielded even though the storage stability before blood application is favorable.

Comparative Embodiment 6

Preparation of an aqueous reagent solution was carried out in the same manner as Embodiment 4 except that, instead of carrying out the preparation of an aqueous reagent solution (pH 6.5) by using 250 mM disodium 1,3-benzene disulfonate (DSB, manufactured by Alfa Aear) in Embodiment 4, the preparation of an aqueous reagent solution was carried out by using 70 mM trisodium 8-methoxy pyrene-1,3,6-trisulfonate (MPTS, manufactured by Sigma Aldrich Company). Herein, as precipitates generated in the aqueous reagent solution (coating solution), it was not possible to produce a sensor chip. The evaluations results are shown in Table 1.

Furthermore, the chemical formula of trisodium 8-methoxy pyrene-1,3,6-trisulfonate (MPTS) is shown below.

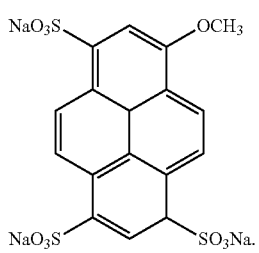

[Chemical Formula 7]

TABLE 1

| | Ionic organic matters (aromatic hydrocarbon) | Chromogenic indicator | Time course | Thermal acceleration test |
|---|---|---|---|---|
| Embodiment 1 | TSN | WST-4 | ⊙ | ○ |
| Embodiment 2 | DSB | WST-4 | ⊙ | ○ |
| Embodiment 3 | BS | WST-4 | ○ | ○ |
| Embodiment 4 | DSB | Tetrazolium salt A | ⊙ | ○ |
| Comparative Embodiment 1 | None | WST-4 | X | X |
| Comparative Embodiment 2 | MOPS | WST-4 | ○ | X |
| Comparative Embodiment 3 | Sodium isethionate | WST-4 | ○ | X |
| Comparative Embodiment 4 | Phosphate buffer solution | WST-4 | ○ | X |
| Comparative Embodiment 5 | Trehalose | WST-4 | X | ○ |
| Comparative Embodiment 6 | MPTS | Tetrazolium salt A | Precipitate was generated in aqueous reagent solution (coating solution) | |

Furthermore, the evaluation criteria for the results of "Absorbance (amount of color development) measurement (time course) after analyte application" and "Absorbance measurement after thermal acceleration test" in Table 1 are as described below.

<Absorbance (Time Course (Amount of Color Development)) Measurement After Analyte Application>

⊙: Within 10 seconds, 90% or more of the reaction end point underwent the reaction ○: Within 10 seconds, 60% or more but less than 90% of the reaction end point underwent the reaction x: Within 10 seconds, less than 60% of the reaction end point underwent the reaction <Absorbance Measurement After Thermal Acceleration Test>

○: Blank increase after storage at 60° C. for 3 days is less than 0.1 x: Blank increase after storage at 60° C. for 3 days is 0.1 or more

According to comparison of Embodiments 1 to 4, in which a blood glucose measurement reagent containing an aromatic hydrocarbon having at least one sulfonic acid group is used, with Comparative Embodiments 1 to 6 in which a blood glucose measurement reagent containing an aromatic hydrocarbon having at least one sulfonic acid group is not used, it was found that, by using a blood glucose measurement reagent containing an aromatic hydrocarbon having at least one sulfonic acid group, the risk of having color development before blood application can be prevented or reduced.

According to comparison of Embodiments 1, 2 and 4, in which a blood glucose measurement reagent containing an aromatic hydrocarbon having at least two sulfonic acid groups is used, with Comparative Embodiment 3 in which a blood glucose measurement reagent containing an aromatic hydrocarbon having one sulfonic acid group is used, by using a blood glucose measurement reagent containing an aromatic hydrocarbon having at least two sulfonic acid groups, not only the risk of having color development before blood application can be prevented or reduced but also the color development speed after blood application can be further increased. Furthermore, according to comparison of Embodiments 1, 2 and 4 with Comparative Embodiment 2, it was found that the blood glucose measurement reagent substantially not added with any buffer and containing an aromatic hydrocarbon having at least two sulfonic acid groups shows not only the prevented or reduced risk of having color development before blood application but also further increased color development speed after blood application.

The present disclosure relates to a blood glucose measurement reagent, a sensor chip, and a blood glucose meter set, and in particular, a blood glucose measurement reagent, a sensor chip, and a blood glucose meter set that can prevent or reduce the risk of color development before blood application and also can increase the color development speed after blood application even when the blood as an analyte is whole blood.

REFERENCE NUMERAL LIST

1: First base
2: Second base
3: Adhesion part
4: Adhesion part
10: Supply port
20: Flow part
21: Opening part
22: Mounting part
23: Mounting hole
24: Optical measurement part
25: Processing part
26: Eject pin
30: Reagent layer (Reagent)
31: Light illuminating part
32: Light receiving part
33: Illumination light
41: First space
42: Second space
51: First light illuminating element 52: Second light illuminating element
100: Sensor chip
110: Blood glucose meter
111: Display
112: Power button
113: Operation button
114: Release lever
500: Blood glucose meter set

What is claimed is:

1. A blood glucose measurement reagent comprising:
  glucose dehydrogenase;
  a chromogenic indicator; and
  an aromatic hydrocarbon selected from disodium 1,3-benzene disulfonate and trisodium naphthalene-1,3,6-trisulfonate.

2. The blood glucose measurement reagent of claim 1, wherein the reagent does not comprise a buffer.

3. The blood glucose measurement reagent of claim 1, wherein the aromatic hydrocarbon is disodium 1,3-benzene disulfonate.

4. The blood glucose measurement reagent of claim 1, wherein the aromatic hydrocarbon is trisodium naphthalene-1,3,6-trisulfonate.

5. The blood glucose measurement reagent of claim 2, wherein the aromatic hydrocarbon is disodium 1,3-benzene disulfonate.

6. The blood glucose measurement reagent of claim 2, wherein the aromatic hydrocarbon is trisodium naphthalene-1,3,6-trisulfonate.

7. The blood glucose measurement reagent of claim 1, wherein the chromogenic indicator is a tetrazolium salt.

8. The blood glucose measurement reagent of claim 2, wherein the chromogenic indicator is a tetrazolium salt.

9. The blood glucose measurement reagent of claim 1, wherein the content of the aromatic hydrocarbon is 30% by mol or more.

10. The blood glucose measurement reagent of claim 2, wherein the content of the aromatic hydrocarbon is 30% by mol or more.

11. The blood glucose measurement reagent of claim 1, wherein the content of the chromogenic indicator is 5% by mol or more.

12. The blood glucose measurement reagent of claim 2, wherein the content of the chromogenic indicator is 5% by mol or more.

13. The blood glucose measurement reagent of claim 1, wherein the aromatic hydrocarbon is at a content of 50% by mol or more, and wherein the chromogenic indicator is a tetrazolium salt at a content of 15% by mol or more.

14. The blood glucose measurement reagent of claim 2, wherein the aromatic hydrocarbon is at a content of 50% by mol or more, and wherein the chromogenic indicator is a tetrazolium salt at a content of 15% by mol or more.

15. The blood glucose measurement reagent of claim 1, wherein the aromatic hydrocarbon is at a concentration of 100 mM or more, and wherein the chromogenic indicator is a tetrazolium salt at a concentration of 50 mM or more.

16. The blood glucose measurement reagent of claim 2, wherein the aromatic hydrocarbon is at a concentration of 100 mM or more, and wherein the chromogenic indicator is a tetrazolium salt at a concentration of 50 mM or more.

17. A method of measuring blood glucose comprising contacting a blood sample with a blood glucose measurement reagent according to claim 1.

18. A method of measuring blood glucose comprising contacting a blood sample with a blood glucose measurement reagent according to claim 2.

* * * * *